United States Patent
Joshi

(10) Patent No.: US 6,575,961 B2
(45) Date of Patent: Jun. 10, 2003

(54) FLUID DELIVERY DEVICE AND ASSOCIATED METHOD

(75) Inventor: Ashok V. Joshi, Salt Lake City, UT (US)

(73) Assignee: Microlin, L.C., Salt Lake City, UT (US)

(*) Notice: Subject to any disclaimer, the term of this patent is extended or adjusted under 35 U.S.C. 154(b) by 56 days.

(21) Appl. No.: 09/788,824

(22) Filed: Feb. 20, 2001

(65) Prior Publication Data

US 2002/0156461 A1 Oct. 24, 2002

(51) Int. Cl.[7] .............................................. A61K 9/22
(52) U.S. Cl. .................... 604/891.1; 604/141; 424/438
(58) Field of Search ................. 604/892.1, 141, 604/131, 890.1, 891.1; 424/438, 424, 425, 473

(56) References Cited

U.S. PATENT DOCUMENTS

| | | | | |
|---|---|---|---|---|
| 3,732,865 A | * | 5/1973 | Higuchi et al. | 424/433 |
| 3,946,734 A | * | 3/1976 | Dedrick et al. | 424/424 |
| 3,995,632 A | * | 12/1976 | Nakano et al. | 222/95 |
| 4,209,014 A | * | 6/1980 | Sefton | 128/DIG. 1 |
| 4,350,271 A | * | 9/1982 | Eckenhoff | 222/386.5 |
| 4,552,561 A | | 11/1985 | Eckenhoff et al. | 604/891.1 |
| 4,675,174 A | * | 6/1987 | Eckenhoff | 424/438 |
| 4,717,566 A | * | 1/1988 | Eckenhoff et al. | 424/438 |
| 4,717,718 A | * | 1/1988 | Eckenhoff et al. | 424/438 |
| 4,734,092 A | | 3/1988 | Millerd | 604/67 |
| 4,772,474 A | * | 9/1988 | Eckenhoff et al. | 424/438 |
| 4,915,949 A | * | 4/1990 | Wong et al. | 424/438 |
| 5,062,841 A | * | 11/1991 | Siegel | 424/423 |
| 5,499,979 A | * | 3/1996 | Wong et al. | 424/438 |

OTHER PUBLICATIONS

Publication entitled "Handbook of Batteries, Second Edition" at Chapter 13, "Zinc–Air Cells," by Steven F. Bender et al. (available from McGraw–Hill Inc.).

* cited by examiner

Primary Examiner—Patrick Brinson
(74) Attorney, Agent, or Firm—Factor & Partners

(57) ABSTRACT

A fluid delivery device comprising a chamber or electrode, wherein the chamber or electrode is capable of containing a chemical and/or electrochemical reagent which expands upon a chemical reaction of the same. The expansion, in turn, displaces a displaceable member which facilitates delivery of fluid from an associated reservoir.

42 Claims, 1 Drawing Sheet

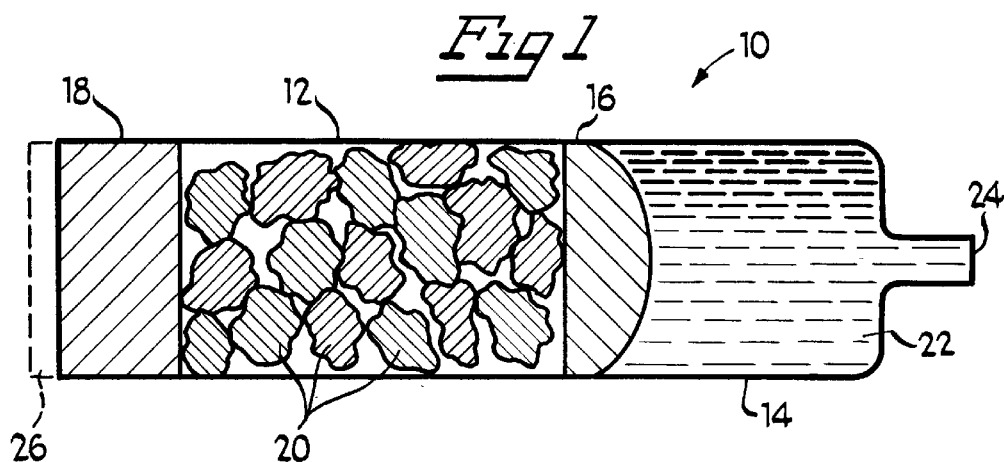
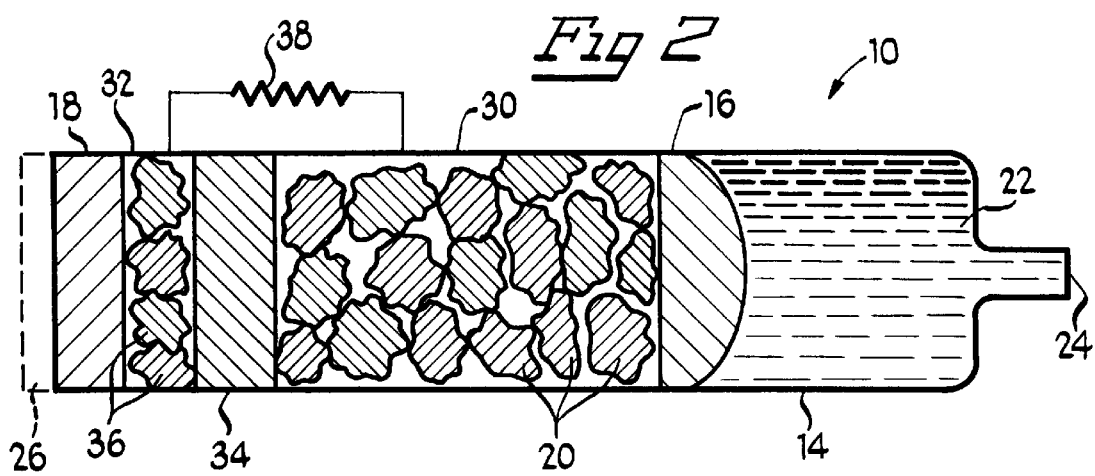
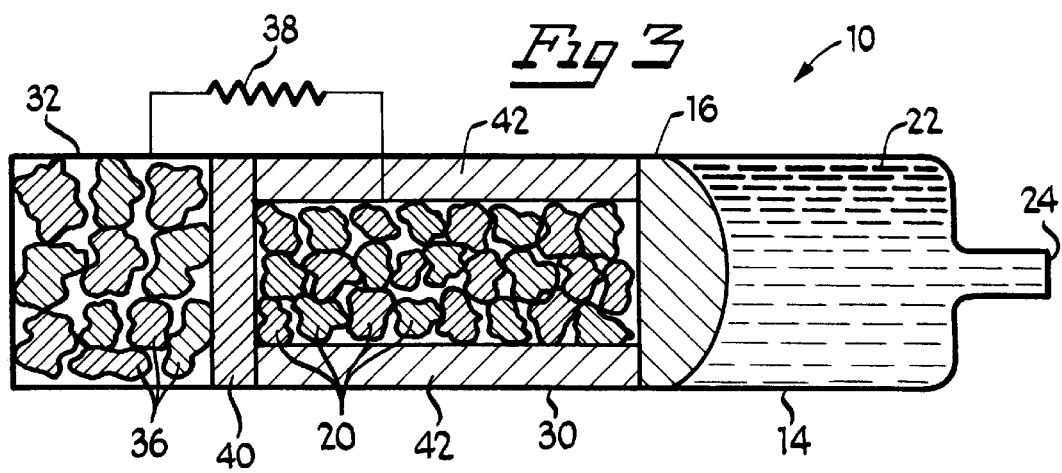

FLUID DELIVERY DEVICE AND ASSOCIATED METHOD

BACKGROUND OF THE INVENTION

1. Field of the Invention

The present invention relates in general to a fluid delivery device, and more particularly, to a fluid delivery device which includes a chemical/electrochemical reagent that expands upon a chemical/electrochemical reaction, such as corrosion, oxidation, reduction, etcetera, thereby generating pressure, and, in turn, delivering a predetermined fluid.

2. Background Art

In many situations it is necessary or desirable to administer relatively small amounts of medicaments, medicines, and/or other pharmaceutical fluids to a patient's body over a relatively long period of time. For example, heparin is administered to a patient in need thereof by an intravenous "drip" procedure. Other medicines which may be administered over long periods of time include antiarrhythmics, streptokinase, vitamins, hormones, and corticosteriods. Other examples of medicines that can benefit from prolonged delivery periods include analgesics, anesthetics, antibiotics, cytostatics, and cytotoxics.

The above-identified medicines can be administered intermittently by bolus injection or continuously by gravity dispensers. Bolus injections may, however, imperfectly match the patient's actual requirements and subject the patient to larger dosages of drugs than required as well as frequent needle insertion. Continuous drug delivery through gravity dispensers may limit the patient's lifestyle by tethering him or her to the familiar intravenous drip apparatus. Furthermore, the dispensing rate is not always constant.

Portable units to deliver medicines have been developed that employ mechanical pumps, pressurized gas or the property of an elastic material to return to its original shape. The mechanical pumps use electrical or clockwork motors. The pressurized devices use elastic, inflated balloons or the vapor pressure of a volatile propellant. These devices suffer from many of the drawbacks of the gravity dispensers. Although portable, they generally remain bulky. The mechanical units have numerous moving parts subject to wear and are relatively expensive. They also may have difficulty dispensing small volumes of liquid accurately and precisely.

Gas generating and osmotic devices have been developed that are both portable and somewhat accurate for dispensing small volumes. These gas generating methods include electrolytic cells, Galvanic cells, and oxygen pumps.

An osmotic pump involves imbibing water or another driving fluid. The pump consists of three chambers: a salt chamber, a water chamber, and a drug chamber. The salt and water chambers are separated by a semi-permeable membrane. This membrane is permeable to water but impermeable to salt. The drug chamber is separated from the other two by a flexible diaphragm. Water imbibes osmotically into the salt chamber creating an osmotic pressure which, in turn, exerts a force on the diaphragm thus expelling the drug.

An electrolytic cell comprises a pair of electrodes suspended in an electrolyte. When voltage is applied to the electrodes, the electrolyte gives off a gas which exerts a force on a diaphragm or piston thus expelling the drug.

A Galvanic cell is essentially a metal/electrolyte cell where hydrogen gas is created by reaction of metal with electrolyte thus completing the contact between metal and cathode. The anode and cathode are connected through a resistor. The resistor regulates the current passed through the cell which directly regulates the production of gas.

An oxygen pump transports oxygen from one side of a membrane to the other. Electrodes are placed on opposite surfaces of an electrolytic membrane. Then a voltage gradient is established across the electrolytic membrane. Oxygen is ionized at the first electrode and passes through the membrane where it is reconverted into oxygen at the second electrode. This oxygen can be captured to provide pumping action through the inflation of a bag.

Portable drug delivery systems have been described. For example, U.S. Pat. No. 4,552,561 to Eckenhoff et al. (Nov. 12, 1985) discloses a rigid, tapered housing that is affixed to the wearer by an annular adhesive overlay. Enclosed within the housing is a chamber for the medicament, an imbibing pump, and a traditional needle. One drawback of such a system is that a rigid housing may not easily conform to the contours of the user's body. Another problem is that the flow rate of an osmotic pump varies with temperature. A change in body or external temperature could have the undesirable effect of changing the medicament flow. In addition, in order to vary the medicament flow, it may be necessary to provide numerous osmotic pumps with differing outputs, or hydrogels with different osmotic properties, or various impermeable membranes to partially preclude the osmotic pump. These limitations make it difficult for the patient to use and control such devices. Osmotic pumps also require charging (the time required for liquid to diffuse through the semipermeable membrane and begin dissolving the osmagent at steady state) which delays the delivery of the medicament and which limits their suitability for instantaneous or emergency use.

U.S. Pat. No. 4,734,092 to Millerd (Mar. 29, 1988) discloses a flexible housing that is attached to the subject by an adhesive surface incorporated on the housing. Enclosed in the housing is a pump module, a cannula, and a fluid conduit passageway in the form of a spirally wrapped tube. The pump transports atmospheric oxygen into the tube. Such pumping creates a pressure which drives the medicament through the cannula. An oil slug separates the medicament and oxygen. The device is actuated by removing a peel tab and rotating the pump so that the output of the pump aligns with the input of the spiraled tube. The flow can be controlled by varying the current to the pump with a potentiometer. One drawback of such a device is the use of added components for a filtering system of hydrophobic and hydrophilic membranes to keep oil and oxygen from being administered to the patient. Thus, the hydrophobic membrane keeps the medicament in the device while allowing the oxygen to escape. The hydrophilic membrane allows medicament to pass into the body while obstructing oxygen. The hydrophilic membrane is of limited porosity so that it also impedes oil. Another disadvantage of this device is the protrusion of the cannula while in the storage or non-use stage. This exposes the device to possible damage and contamination. Also, a protruding needle does little to re-assure a traumatized or needle-phobic patient. An additional drawback is the difficulty in manufacturing a device with a spiral wrapped tube.

Another development in delivery systems is the transdermal patch. The patch is attached to the skin by an adhesive surface. Medicine then passes through the patch and the skin. A drawback of transdermal drug delivery technology is that certain molecules are very difficult to administer in effective doses. In addition, control of the drug administration can be limited. Moreover, in the case of iontophoretic drug delivery, competing ions can be problematic.

While the above-identified fluid delivery devices have become publicly known, there remains a substantial commercial demand for a simple, economical fluid delivery device or system which either monitored or unmonitored, delivers a fluid, accurately and precisely, at a relatively constant adjustable and controlled rate over an industrially recognized extended period of time.

SUMMARY OF THE INVENTION

The present invention is directed to a fluid delivery device comprising: (a) a reaction chamber, wherein the reaction chamber is capable of containing a chemical reagent which expands upon a chemical reaction; (b) a membrane associated with the reaction chamber in a fixed position; (c) a displaceable member positioned between the reaction chamber and a reservoir, wherein the displaceable member is displaced upon expansion of the chemical reagent; and (d) a reservoir, wherein the reservoir is capable of containing a fluid which is delivered upon displacement of the displaceable member.

In a preferred embodiment of the present invention, the reaction chamber includes a chemical reagent which expands upon a chemical reaction, such as corrosion, oxidation, reduction, etc. In this embodiment, the chemical reagent may be selected from the group consisting of: metals and other chemical compounds, such as metals including Fe, Zn, Al, Ca, Mg, their alloys and compounds and mixtures thereof.

In another preferred embodiment of the present invention, the membrane is oxygen and moisture permeable and optionally includes a cover member which, upon its removal, allows oxygen and/or moisture into the reaction chamber.

In yet another preferred embodiment of the invention, the displaceable member may be selected from the group consisting of a piston, bladder, diaphragm, plunger, and combinations thereof.

In accordance with the present invention, the reservoir contains a fluid, such as a medicament, lubricant, surfactant, disinfectant, deodorant, pesticide, insecticide, herbicide, and mixtures thereof.

The present invention is further directed to a fluid delivery device comprising: (a) a reaction chamber which includes at least one of the following: metal, metal alloys, metal compounds, electrolyte solutions, hydrogen scavengers, or mixtures thereof, which expand upon a chemical or electrochemical reaction in combination with or without an osmotic process; (b) a membrane associated with the reaction chamber in a fixed position, wherein the membrane is hydrogen, oxygen and moisture permeable; (c) a displaceable member positioned between the reaction chamber and a reservoir, wherein the displaceable member is displaced as a result of the chemical or electrochemical reaction with the metal, metal alloys, metal compounds and electrolyte solutions or mixtures thereof, in combination with or without an osmotic process; and (d) a reservoir, wherein the reservoir is capable of containing a fluid which is delivered upon displacement of the displaceable member.

In a preferred embodiment of the invention, the reservoir includes one or more apertures.

The present invention is also directed to a fluid delivery device comprising: (a) a reaction chamber, wherein the reaction chamber includes at least one of a metal, metal alloy, metal compounds or combinations thereof, which expands upon chemical and/or eletrochemical reaction; (b) a membrane associated with the reaction chamber in a fixed position, wherein the membrane is hydrogen, oxygen and moisture permeable; (c) a displaceable member positioned between the reaction chamber and a reservoir, wherein the displaceable member is displaced upon expansion of the metal, metal alloy and/or metal compounds with an electrolyte and/or oxygen; and (d) a reservoir, wherein the reservoir contains a fluid which is delivered upon displacement of the displaceable member, the fluid being selected from the group consisting of a medicament, lubricant, surfactant, disinfectant, deodorant, pesticide, insecticide, herbicide, and mixtures thereof.

The present invention is further directed to a fluid delivery device comprising: (a) a first electrode having a first active material, wherein the first active material expands upon a chemical and/or electrochemical reaction; (b) a second electrode having a second active material; (c) a separator positioned between the first and second electrodes; (d) a membrane associated with the second electrode in a fixed position; (e) a displaceable member positioned between the first electrode and a reservoir, wherein the displaceable member is displaced upon expansion of the first active material; and (f) a reservoir, wherein the reservoir is capable of containing a fluid which is delivered upon displacement of the displaceable member.

In a preferred embodiment of the present invention, the first electrode comprises an anode which may be fabricated from metal, for example, Zn, Fe, Al, Ca, Mg, or mixtures thereof and the second electrode comprises, for example, a cathode which may comprise air, or an electrode, such as a carbon Teflon composite electrode which facilitates an oxidation reaction with the first electrode.

Preferably, a resistor is provided in electrical communication with the first electrode to controllably regulate discharge rate of the anode. Such discharge rates will be readily discernable from those having ordinary skill in the art, as exemplified in the publication entitled "Handbook of Batteries, Second Edition" at Chapter 13, "Zinc/Air Cells," Steven F. Bender, et al. (available from McGraw-Hill, Inc.).

The present invention is also directed to a fluid delivery device comprising: (a) a first electrode having a first active material, wherein the first active material expands upon a chemical and/or electrochemical reaction; (b) a second electrode having a second active material; (c) an electrolyte positioned between the first and second electrodes in a fixed position; (d) a displaceable member positioned between the first electrode and a reservoir, wherein the displaceable member is displaced upon expansion of the first active material; and (e) a reservoir, wherein the reservoir is capable of containing a fluid which is delivered upon displacement of the displaceable member.

In a preferred embodiment of the present invention, the first electrode comprises a cathode which may be fabricated from a metal halide, metal chalconide, such as $PbI_2$, $BiI_3$, PbS, $Bi_2S_3$, etc., the second electrode comprises an anode which may be fabricated from single valent metal, such as Li, Na, Cu, Ag, Au, etc., and the electrolyte comprises a rigid solid phase electrolyte fabricated from a lithium ion conductor, for example, LiI—$Al_2O_3$, lithium beta aluminum and a lithium conducting polymer electrolyte.

BRIEF DESCRIPTION OF THE DRAWINGS

The invention will now be described with reference to the drawings wherein:

FIG. 1 of the drawings is a cross-sectional schematic representation of a first embodiment of a fluid delivery device fabricated in accordance with the present invention;

FIG. 2 of the drawings is a cross-sectional schematic representation of a second embodiment of a fluid delivery device fabricated in accordance with the present invention; and FIG. 3 of the drawings is a cross-sectional schematic representation of a third embodiment of a fluid delivery device fabricated in accordance with the present invention.

DETAILED DESCRIPTION OF THE INVENTION

While this invention is susceptible of embodiment in many different forms, there is shown in the drawings and will herein be described in detail several specific embodiments with the understanding that the present disclosure is to be considered as an exemplification of the principles of the invention and is not intended to limit the invention to the embodiments illustrated.

It will be understood that like or analogous elements and/or components, referred to herein, may be identified throughout the drawings with like reference characters.

Referring now to the drawings and to FIG. 1 in particular, a first embodiment of fluid delivery device 10 is shown, which generally comprises reaction chamber 12, reservoir 14, displaceable member 16, and membrane 18. It will be understood that the term "fluid" is herein defined as a liquid, gel, paste, or other semi-solid or solid state material that is capable of being delivered out of a reservoir. It will be further understood that FIG. 1 is merely a schematic representation of fluid delivery device 10. As such, some of the components have been distorted from their actual scale for pictorial clarity.

Reaction chamber 12 is capable of containing chemical and/or electrochemical reagent 20. As will be discussed in greater detail below, reagent 20 expands upon a chemical and/or electrochemical reaction that laterally displaces displaceable member 16, thereby delivering fluid from within reservoir 14. For purposes of the present disclosure, reaction chamber 12 may be fabricated from any one of a number of materials, including metals, glass, natural and synthetic resins and plastics, composites—just to name a few.

Reservoir 14 is capable of containing fluid 22, such as a medicament, lubricant, surfactant, disinfectant, deodorant, pesticide, insecticide, herbicide, or mixtures thereof, which is/are delivered upon displacement of displaceable member 16. Reservoir 14 may include one or more apertures 24 for directing delivery of fluid 22 from fluid delivery device 10. Similar to reaction chamber 12, reservoir 14 may be fabricated from any one of a number of materials, including metals, glass, natural and synthetic plastics, composites— just to name a few.

Displaceable member 16 is positioned between reaction chamber 12 and reservoir 14. Displaceable member 16 is shown in FIG. 1, for illustrative purposes only, as comprising a piston, however, other displaceable members that would be known to those having ordinary skill in the art having the present disclosure before them are likewise contemplated for use, including a bladder, diaphragm, plunger, etcetera.

Membrane 18 is associated with the reaction chamber 12 in a fixed position. In particular, membrane 18 emanates contiguously from the end of reaction chamber 12 distal displaceable member 16. Membrane 18 is fixed in position so that upon expansion of reagent 20, only displaceable member 16 is displaced. For purposes of the present disclosure, membrane 18 is oxygen, hydrogen and moisture permeable. The permeability of the membrane serves two functions. First, it allows air and moisture to enter the reaction chamber and, in turn, participate in a chemical and/or electrochemical reaction. Second, it allows gaseous byproducts of the reaction to be expelled from the reaction chamber without undesirably displacing displaceable member 16. Examples of suitable materials for membrane 18 include, among other, metal meshes, natural and synthetic fabrics, natural and synthetic resins and plastics with or without visible apertures, etcetera.

Cover member 26 may be optionally applied onto membrane 18. Cover member 26 is substantially impermeable to air and/or moisture and serves to protect reagent 20 from undesirable exposure to air and/or moisture, for example, during storage or transportation of the device. Cover member 26 may be fabricated from numerous materials. The only limitation is that the material must be substantially impermeable to air and/or moisture, yet permeable to hydrogen.

In operation, fluid delivery device 10 can deliver fluid 22 in accordance with the following process. First, if fluid delivery device 10 includes cover member 26, the cover member is removed so that oxygen from the air and/or moisture can pass through membrane 18 and into reaction chamber 12. Once oxygen from the air and/or moisture enter reaction chamber 12 a chemical and/or electrochemical reaction, such as corrosion, oxidation, occurs with chemical reagent 20. For purposes of the present disclosure, reagent 20 may include: metals, such as transition metals including iron, iron alloys, as well as other metals and their alloys and compounds and electrolyte solutions and mixtures thereof. Using iron as an example, the moisture from the oxidative atmosphere reacts with the iron to form several products which occupy more space than their unreacted counter parts. Table I below provides at least some of the known reactions, wherein the products occupy more space than the iron reagent:

TABLE I

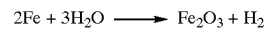
$2Fe + 3H_2O \longrightarrow Fe_2O_3 + H_2$

$3Fe + 4H_2O \longrightarrow Fe_3O_4 + 4H_2$

$Fe + 2H_2O \longrightarrow FeOOH + 3/2H_2$

$Fe + 3H_2O \longrightarrow Fe(OH)_3 + 3/2H_2$

As can be seen one or more of the following products are formed when iron reacts with moisture in an oxidative environment. The products occupy more space than their reagent counter parts because oxygen is inserted into the iron lattice.

While the chemical and/or electrochemical reaction is occurring, pressure is being generated within reaction chamber 12 due to the expanded geometries of the products. The generated pressure, in turn, imparts a force upon displaceable member 16—the only movable component. Displaceable member 16 is displaced laterally away from reaction chamber 12, which controllably expels fluid from reservoir 14. It will be understood that the above-identified device and process enables a controlled delivery of a fluid over an extended period of time at a relatively constant rate inasmuch as the pressure generated is proportional to the rate of reaction.

As yet a further example, and with respect to the embodiment of FIG. 1, reagent 20 may comprise an iron and salt mixture. When cover member 26 is removed, and the device is placed, for example, in a body cavity of a living being (where there is plenty of moisture and oxygen), membrane 18 transports moisture and oxygen to composite reagent 20. As a result, iron, in the composite reagent, starts to corrode in the presence of salt and moisture. As the iron starts to corrode, moisture is also pulled/drawn in from outside of the device through membrane 18. Iron either reacts with oxygen (pulled in from outside of the device), or it reacts with the moisture which is also pulled in by salt present in reagent 20. Either way, iron gets converted into a mixture of oxides and hydroxides under these conditions—thereby increasing its volume.

Besides the above-referenced expansion of iron, salt also contributes to volume expansion as it pulls water/moisture from the body cavity. As the volume expands within the reaction chamber (due to the conversion of iron and the pulling of moisture by the salt), the expansion causes plunger 16 to move so that fluid 22 in chamber 14 expels through orifice 24. The rate of expansion is equal to the rate of delivery of fluid which, in turn, depends on the composition of the iron and salt mixture as well as the membrane and the design of the device.

Referring now to FIG. 2, a second embodiment of drug delivery device 10 is shown which generally comprises reservoir 14, displaceable member 16, membrane 18, first electrode 30, second electrode 32, and separator 34. First electrode 30 and second electrode 34 electrically cooperate to function as an electrochemical cell. It will be understood that reservoir 14, displaceable member 16, and membrane 18 are configured analogously to those previously identified and disclosed relative to FIG. 1.

First electrode 30 is positioned between displaceable member 16 and separator 34, and includes first chemical and/or electrochemical reagent/active material 20. In accordance with the present embodiment, first electrode 30 is an anode fabricated from Zn, Fe, Al, Ca, Mg, their alloys or compounds or mixtures thereof. It will be understood that numerous other active materials are likewise contemplated for use.

Second electrode 32 is positioned between membrane 18 and separator 34, and includes second chemical and/or electrochemical reagent/active material 36. In accordance with the present embodiment, second electrode 32 is a cathode fabricated from air or the native atmosphere.

Separator 34 is positioned between the first and second electrodes 30 and 32, respectively, and serves to isolate the electrodes to prevent short circuiting.

Fluid delivery device 10 may also include resistor 38 which is in electrical communication with first electrode 30. Resistor 38 controls the rate of reaction and may comprise any one of a number of values depending primarily upon the particular application.

In operation, fluid delivery device 10 of FIG. 2 can deliver fluid 22 in accordance with the following process. First, if fluid delivery device 10 includes cover member 26, the cover member is removed so that air and/or moisture 36 can pass through membrane 18 and into second electrode 32. Air and/or moisture 36, which serves as the second active material, then migrates to first electrode 30 and reacts with first active material 20, which is in the present case a zinc composition. In particular the zinc composition is oxidized to ZnO upon discharge. The rate of discharge will depend upon the value of resistor 38.

While the electrochemical cell is discharging, pressure is being generated within first electrode 30 as a result of the formation of zinc oxide from zinc. The generated pressure, in turn, imparts a force upon displaceable member 16—the only movable component. Displaceable member 16 is displaced laterally away from first electrode 30, which controllably expels fluid 22 from reservoir 14. It will be understood that the above-identified device and process enables a controlled delivery of a fluid over an extended period of time at a relatively constant rate inasmuch as the pressure generated is proportional to the rate of reaction.

As yet a further example, and with respect to the embodiment of FIG. 2, the electrochemical reagent comprises an electrochemical cell. The cell includes an anode material (20) in reaction chamber 30, separator 34 and carbon Teflon composite cathode 36. When cover member 26 is removed and the device is activated by connecting the appropriate resistor between cathode 36 and anode 20, then the oxygen and the water from outside of the device will transport through membrane 18, which is permeable to hydrogen, oxygen and water. Anode material 20 comprises a gel or zinc alloy and salt, while separator 34 comprises a microporous polypropylene membrane. Cathode 36 comprises a porous carbon and Teflon composite membrane.

As the cathode, oxygen and water ionize to form hydroxyl ions, while at the anode, such hydroxyl ions react with zinc to form zinc oxide. When the zinc transforms into zinc oxide, there is an expansion of approximately 60%. Depending upon the current between the anode and the cathode, the rate of expansion of the anode will force moveable plunger 16 to move, thereby causing fluid 22 to expel through orifice 24. In the absence of oxygen availability, the zinc anode will react with the salt electrolyte itself to form hydrogen and zinc oxide. As hydrogen forms, it escapes from the device either through membrane 18 or through the walls of the device. Additionally, a hydrogen scavenger, such as palladium, could be introduced in the anode so that hydrogen is absorbed as it is formed.

Referring now to FIG. 3, a third embodiment of drug delivery device 10 is shown which generally comprises reservoir 14, displaceable member 16, first electrode 30, second electrode 32, and electrolyte 40. First electrode 30, second electrode 32, and electrolyte 40 electrically cooperate to serve as an internally supported electrochemical cell. Inasmuch as the electrochemical cell is internally supported it does not require air and/or moisture from its surroundings. It will be understood that reservoir 14, displaceable member 16, and membrane 18 are configured analogously to those previously identified and disclosed relative to FIGS. 1 and 2.

First electrode 30 is positioned between displaceable member 16 and electrolyte 40, and includes first chemical reagent/active material 20. In accordance with the present embodiment, first electrode 30 is a cathode fabricated from a metal halide, such as $PbI_2$. Of course, numerous other materials suitable for use as cathodic components are likewise contemplated for use.

Second electrode 32 serves as one end of the device and is positioned adjacent to electrolyte 40. Second electrode 32 includes second chemical reagent/active material 36. In accordance with the present embodiment, second electrode 30 is an anode fabricated from an alkali metal, such as lithium, or an alkaline earth metal.

Electrolyte 40 is positioned between the first and second electrodes 30 and 32, respectively, and serves as a conductive medium. Electrolyte 40 is preferably a solid phase electrolyte fabricated from, for example, a metal halide alumina salt, such as $LiI$—$Al_2O_3$.

Insulator 42 is positioned between displaceable member 16 and electrolyte 40, and serves to preclude first electrode 30 from contacting a portion of the device which would cause a short circuit.

Fluid delivery device 10 may also include resistor 38 which is in electrical communication with first electrode 30. Resistor 38 controls the rate of reaction and may comprise any one of a number of values depending primarily upon the particular application.

In operation, fluid delivery device 10 of FIG. 3 can deliver fluid 22 in accordance with the following process. Discharge of the internally supported electrochemical cell is initiated in a conventional manner. Reduction at the cathode or first electrode results in the conversion of lead iodide to lithium iodide and lead. Inasmuch as the products of the reduction (i.e. LiI and Pb) occupy a greater volume than the reagent, $PbI_2$, pressure is generated which in turn, imparts a force upon displaceable member 16—the only movable component. Displaceable member 16 is displaced laterally away from first electrode 30, which controllably expels fluid 22 from reservoir 14. It will be understood that the above-identified device and process enables a controlled delivery of a fluid over an extended period of time at a relatively constant rate inasmuch as the pressure generated is proportional to the rate of reaction.

The foregoing description merely explains and illustrates the invention and the invention is not limited thereto except insofar as the appended claims are so limited, as those skilled in the art who have the disclosure before them will be able to make modifications without departing the scope of the invention.

What is claimed is:

1. A fluid delivery device, comprising:
   a reaction chamber, wherein the reaction chamber includes a chemical reagent which expands upon a chemical and/or electrochemical reaction;
   a membrane associated with the reaction chamber in a fixed position;
   a displaceable member positioned between the reaction chamber and a reservoir, wherein the displaceable member is displaced upon expansion of the reagent; and
   a reservoir, wherein the reservoir is capable of containing a fluid which is delivered upon displacement of the displaceable member;
   wherein the chemical reaction is selected from the group consisting of corrosion, oxidation, and/or reduction.

2. The fluid delivery device according to claim 1, wherein the membrane is oxygen and moisture permeable.

3. The fluid delivery device according to claim 1, wherein the membrane further includes a cover member which, upon removal, allows oxygen and/or moisture into the reaction chamber.

4. The fluid delivery device according to claim 1, wherein the displaceable member is selected from the group consisting of a piston, bladder, diaphragm, plunger, and combinations thereof.

5. The fluid delivery device according to claim 1, wherein the reservoir contains a fluid selected from the group consisting of a medicament, lubricant, surfactant, disinfectant, deodorant, pesticide, insecticide, herbicide, and mixtures thereof.

6. The fluid delivery device according to claim 1, wherein the reservoir includes one or more apertures.

7. The fluid delivery device according to claim 1, wherein the chemical reagent is selected from the group consisting of a metal, a metal alloy, a metal compound, and mixtures thereof.

8. The fluid delivery device according to claim 1, wherein the reaction chamber additionally includes an electrochemical reagent which expands upon an electrochemical reaction.

9. A fluid delivery device, comprising:
   a reaction chamber, wherein the reaction chamber includes a chemical reagent which expands upon a chemical and/or electrochemical reaction;
   a membrane associated with the reaction chamber in a fixed position;
   a displaceable member positioned between the reaction chamber and a reservoir, wherein the displaceable member is displaced upon expansion of the reagent; and
   a reservoir, wherein the reservoir is capable of containing a fluid which is delivered upon displacement of the displaceable member;
   wherein the chemical reagent is selected from the group consisting of a metal, a metal alloy, a metal compound, and mixtures thereof.

10. The fluid delivery device according to claim 9, wherein the reaction chamber additionally includes an electrochemical reagent which expands upon an electrochemical reaction.

11. The fluid delivery device according to claim 10, wherein the electrochemical reagent is selected from the group consisting of redox reagents.

12. The fluid delivery device according to claim 11, wherein the electrochemical reagent expands upon a discharge reaction.

13. The fluid delivery device according to claim 10, wherein the electrochemical reagent expands upon a discharge reaction.

14. The fluid delivery device according to claim 10, wherein the chemical and/or electrochemical reagent is selected from the group consisting of hydrogen scavengers, Fe, Zn, Li, Na, Ca, Mg, Al, their alloys and compounds mixed with electrolyte solution.

15. The fluid delivery device according to claim 9, wherein the membrane is oxygen and moisture permeable.

16. The fluid delivery device according to claim 9, wherein the membrane further includes a cover member which, upon removal, allows oxygen and/or moisture into the reaction chamber.

17. The fluid delivery device according to claim 9, wherein the displaceable member is selected from the group consisting of a piston, bladder, diaphragm, plunger, and combinations thereof.

18. The fluid delivery device according to claim 9, wherein the reservoir contains a fluid selected from the group consisting of a medicament, lubricant, surfactant, disinfectant, deodorant, pesticide, insecticide, herbicide, and mixtures thereof.

19. The fluid delivery device according to claim 9, wherein the reservoir includes one or more apertures.

20. A fluid delivery device, comprising:
    a reaction chamber, wherein the reaction chamber is capable of containing at least one of a chemical and electrochemical reagent which expands upon a chemical and or electrochemical reaction;
    a membrane associated with the reaction chamber in a fixed position;
    a displaceable member positioned between the reaction chamber and a reservoir, wherein the displaceable member is displaced upon expansion of the reagent; and
    a reservoir, wherein the reservoir is capable of containing a fluid which is delivered upon displacement of the displaceable member,
    wherein the electrochemical reagent is selected from the group consisting of redox reagents.

21. The fluid delivery device according to claim 20, wherein the reaction chamber includes a chemical reagent which expands upon a chemical and/or electrochemical reaction.

22. The fluid delivery device according to claim 21, wherein the chemical reaction is selected from the group consisting of corrosion, oxidation, and/or reduction.

23. The fluid delivery device according to claim 21, wherein the chemical reagent is selected from the group consisting of a metal, a metal alloy, a metal compound, and mixtures thereof.

24. The fluid delivery device according to claim 21, wherein the chemical and/or electrochemical reagent is selected from the group consisting of hydrogen scavengers, Fe, Zn, Li, Na, Ca, Mg, Al, their alloys and compounds mixed with electrolyte solution.

25. The fluid delivery device according to claim 20, wherein the electrochemical reagent expands upon a discharge reaction.

26. The fluid delivery device according to claim 20, wherein the membrane is oxygen and moisture permeable.

27. The fluid delivery device according to claim 20, wherein the membrane further includes a cover member which, upon removal, allows oxygen and/or moisture into the reaction chamber.

28. The fluid delivery device according to claim 20, wherein the displaceable member is selected from the group consisting of a piston, bladder, diaphragm, plunger, and combinations thereof.

29. The fluid delivery device according to claim 20, wherein the reservoir contains a fluid selected from the group consisting of a medicament, lubricant, surfactant, disinfectant, deodorant, pesticide, insecticide, herbicide, and mixtures thereof.

30. The fluid delivery device according to claim 20, wherein the reservoir includes one or more apertures.

31. A fluid delivery device, comprising:
 a reaction chamber, wherein the reaction chamber includes a chemical reagent which expands upon a chemical and/or electrochemical reaction;
 a membrane associated with the reaction chamber in a fixed position;
 a displaceable member positioned between the reaction chamber and a reservoir, wherein the displaceable member is displaced upon expansion of the reagent; and
 a reservoir, wherein the reservoir is capable of containing a fluid which is delivered upon displacement of the displaceable member;
 wherein the chemical reagent is selected from the group consisting of hydrogen scavengers, Fe, Zn, Li, Na, Ca, Mg, Al, their alloys and compounds mixed with electrolyte solution.

32. The fluid delivery device according to claim 31, wherein the chemical reaction is selected from the group consisting of corrosion, oxidation, and/or reduction.

33. The fluid delivery device according to claim 31, wherein the chemical reagent is selected from the group consisting of a metal, a metal alloy, a metal compound, and mixtures thereof.

34. The fluid delivery device according to claim 31, wherein the reaction chamber additionally includes an electrochemical reagent which expands upon an electrochemical reaction.

35. The fluid delivery device according to claim 34, wherein the electrochemical reagent is selected from the group consisting of redox reagents.

36. The fluid delivery device according to claim 34, wherein the electrochemical reagent expands upon a discharge reaction.

37. The fluid delivery device according to claim 31, wherein the membrane is oxygen and moisture permeable.

38. The fluid delivery device according to claim 31, wherein the membrane further includes a cover member which, upon removal, allows oxygen and/or moisture into the reaction chamber.

39. The fluid delivery device according to claim 31, wherein the displaceable member is selected from the group consisting of a piston, bladder, diaphragm, plunger, and combinations thereof.

40. The fluid delivery device according to claim 31, wherein the reservoir contains a fluid selected from the group consisting of a medicament, lubricant, surfactant, disinfectant, deodorant, pesticide, insecticide, herbicide, and mixtures thereof.

41. The fluid delivery device according to claim 31, wherein the reservoir includes one or more apertures.

42. A fluid delivery device comprising:
 a reaction chamber which includes at least one of a metal, metal alloy, metal compound, hydrogen scavanger, electrolyte solutions or mixtures thereof which expands upon a chemical or electrochemical reaction in combination with or without an osmotic process;
 a membrane associated with the reaction chamber in a fixed position, wherein the membrane is hydrogen, oxygen and moisture permeable;
 a displaceable member positioned between the reaction chamber and a reservoir, wherein the displaceable member is displaced as a result of the chemical or electrochemical reaction with the metal, metal alloys, metal compounds, electrolyte solutions, hydrogen scavanger, or mixtures thereof, in combination with or without an osmotic process; and
 a reservoir, wherein the reservoir is capable of containing a fluid which is delivered upon displacement of the displaceable member.

* * * * *